(12) United States Patent
Lemchen

(10) Patent No.: US 8,506,292 B2
(45) Date of Patent: Aug. 13, 2013

(54) HIGH/LOW BRACKET PLACEMENTS ON LINGUAL SURFACES

(76) Inventor: Marc S. Lemchen, New York, NY (US)

(*) Notice: Subject to any disclaimer, the term of this patent is extended or adjusted under 35 U.S.C. 154(b) by 0 days.

(21) Appl. No.: 13/070,270

(22) Filed: Mar. 23, 2011

(65) Prior Publication Data

US 2011/0236848 A1 Sep. 29, 2011

Related U.S. Application Data

(60) Provisional application No. 61/317,360, filed on Mar. 25, 2010.

(51) Int. Cl.
*A61C 7/16* (2006.01)
(52) U.S. Cl.
USPC .................................. 433/9; 433/24
(58) Field of Classification Search
USPC ............... 433/2, 20, 24, 8–18, 21; D24/176, D24/180, 182
See application file for complete search history.

(56) References Cited

U.S. PATENT DOCUMENTS

| | | | | |
|---|---|---|---|---|
| 3,477,128 A | * | 11/1969 | Andrews | 433/16 |
| 3,775,850 A | * | 12/1973 | Northcutt | 433/16 |
| 5,954,502 A | * | 9/1999 | Tuenge et al. | 433/16 |
| 7,076,980 B2 | * | 7/2006 | Butscher et al. | 72/21.4 |
| 2001/0038991 A1 | | 11/2001 | Nicola | |
| 2005/0019720 A1 | | 1/2005 | Harima | |
| 2005/0130094 A1 | | 6/2005 | Graham | |
| 2005/0244781 A1 | | 11/2005 | Abels | |
| 2005/0255422 A1 | * | 11/2005 | Cordato | 433/10 |
| 2007/0212659 A1 | * | 9/2007 | Andreiko et al. | 433/24 |
| 2008/0268398 A1 | * | 10/2008 | Cantarella | 433/20 |
| 2009/0017411 A1 | * | 1/2009 | Pospisil et al. | 433/9 |

* cited by examiner

*Primary Examiner* — Cris L Rodriguez
*Assistant Examiner* — Justin O'Donnell
(74) *Attorney, Agent, or Firm* — Marcus C. Dawes; Daniel L. Dawes

(57) ABSTRACT

An orthodontic bracket system used on the anterior lower teeth includes a plurality of alternating high-low brackets which is made up of a subplurality of high brackets and low brackets. The plurality of alternating high-low brackets are fixed to the anterior teeth, namely the subplurality of high brackets is fixed to alternately successive anterior teeth and the low brackets are fixed to other ones of alternately successive anterior teeth. A first orthodontic wire is coupled or attached to the subplurality of high brackets. A second orthodontic wire is coupled or attached to the subplurality of low brackets. The first and second orthodontic wires are selectively bent between selected brackets to which the first and second orthodontic wires are coupled, so that length of the first and second wire between each bracket to which it is coupled is increased, leaving space between brackets for bends formed in the wire.

5 Claims, 1 Drawing Sheet

HIGH/LOW BRACKET PLACEMENTS ON LINGUAL SURFACES

RELATED APPLICATIONS

The present application is related to U.S. Provisional Patent Application, Ser. No. 61/317,360, filed on Mar. 25, 2010, which is incorporated herein by reference and to which priority is claimed pursuant to 35 USC 119.

BACKGROUND OF THE INVENTION

Field of the Invention

The invention relates to the field of orthodontic bracket and wire systems.

BRIEF SUMMARY OF THE INVENTION

The illustrated embodiments of the invention include an orthodontic bracket system on anterior lower teeth. The system includes a plurality of alternating high-low brackets which is made up of a subplurality of high brackets and a subplurality of low brackets. The plurality of alternating high-low brackets are fixed to the anterior teeth, namely the subplurality of high brackets is fixed to alternately successive anterior teeth and the subplurality of low brackets is fixed to other ones of alternately successive anterior teeth. A first orthodontic wire is coupled or attached to the subplurality of high brackets. A second orthodontic wire is coupled or attached to the subplurality of low brackets. The first and second orthodontic wires are selectively bent between selected brackets to which the first and second orthodontic wires are coupled, so that length of the first and second wire between each bracket to which it is coupled is increased, leaving space between brackets for bends formed in the wire. The wires are bent to apply forces to align the teeth in three dimensions. The alternating brackets or slot heights on the brackets result in the increased length of wire between connections to brackets, so that bends can be made without inducing permanent deformations in the wire, since adjustments are continually made in the course of orthodontic treatment. The increased length of wire provides enough space to bend wire without requiring an impractical degree of precision for the placement of the bend along the length of the wire. Otherwise the bend would have to be so small and rigid that engaging the wire would permanently deform it rendering it unusable. Also the length of the wire is sized so that the orthodontist or the robot can make the bend with reasonably sized "grippers" for the robot or pliers for the orthodontist.

The plurality of alternating high-low brackets may be self-ligating brackets, traditional brackets, or another selected type of bracket for use as the plurality of alternating high-low brackets.

The first orthodontic wire coupled to the subplurality of high brackets and the second orthodontic wire coupled to the subplurality of low brackets includes a split or two piece arch of two overlapping segments of the first and second orthodontic wires across an anterior segment of teeth.

The orthodontic bracket system is further combined with a wire bending robot. The first orthodontic wire coupled to the subplurality of high brackets and the second orthodontic wire coupled to the subplurality of low brackets, and selectively bent between selected brackets to which the first and second orthodontic wires are coupled are selective coupled and/or bent by the wire bending robot.

The orthodontic bracket system further includes a bonding pad fixed to each tooth and where the plurality of alternating high-low brackets are sized to selectively be coupled on an upper or lower portion of the bonding pad fixed to each tooth.

The plurality of alternating high-low brackets may in one embodiment be universal brackets arranged and configured to be selectively configured as a high bracket or as a low bracket. The universal brackets each include a sliding mechanism to allow for connection in either a high or low position without any need to remount the bracket on the tooth.

The orthodontic bracket system further includes a compensating bend selectively formed in the first and second orthodontic wires between a cuspid and premolar or between the cuspid and central incisor to allow a high and low anterior segment of the first and second orthodontic wires to return to a plane common to right and left posterior segments of the first and second orthodontic wires extending to right and left premolars and molars respectively.

The first orthodontic wire coupled to the subplurality of high brackets and the second orthodontic wire coupled to the subplurality of low brackets are selectively bent between selected brackets to which the first and second orthodontic wires are coupled and fixed at positions located high or low on alternate teeth respectively.

In one embodiment the cuspid bracket is a bracket with a slot or attachment point for a single wire reflecting the position of the tooth distal to it, or any other predetermined height, or with a double slotted bracket with one slot corresponding to the height of the tooth distal to it or another predetermined height, and the other slot corresponding to the height of the wire coming from the opposing side, so that the wire terminates in the cuspid bracket. A double slotted cuspid bracket with one high slot and one low slot may be used in cases where adequate space exists between the cuspid and lateral for a bend or none is required. In this way in selected cases we could shorten the span of teeth not connected and add rigidity to the anterior segment.

The illustrated embodiments of the invention further extend to a method of installing and employing any one of the above embodiments of the orthodontic bracket system.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
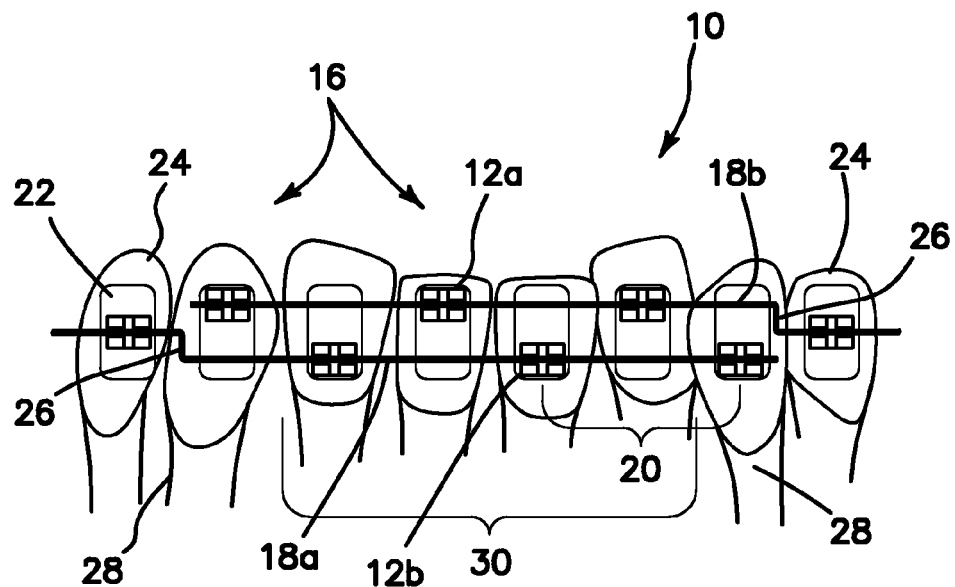
FIG. 1 is a diagram of an illustrated embodiment of the orthodontic bracket system of the invention showing its application to the lower anterior teeth, where the brackets on the lower anterior teeth from cuspid to cuspid are each place on a bonding pad in either a high or low position.

The illustrated embodiment is directed to a lingual or tongue side bracket system as shown in FIG. 1. However, it must be understood the spirit and scope of the invention also includes buccal or cheek-side bracket systems as well. For the lower anterior teeth, namely in the region from cuspid to cuspid which typically includes the four incisors 30 and the two cuspids 28, wire bending robots have a most difficult time bending wires, because the teeth are small and the brackets are close together, especially with crowded or rotated teeth. In such cases, the robotic grippers are typically not small or fine enough to efficiently or effectively operate. Such bending robots are well known to the art and one example is shown in "Robot and method for bending orthodontic archwires and other medical devices," U.S. Pat. No. 7,076,980, incorporated herein by reference.

The illustrated embodiment provides alternating brackets 12a and 12b for this difficult region. High-low bracket placement on every other tooth 16 (cuspid 28 to cuspid 28) more than doubles the length of that portion 20 of the wire 18a, 18b between each connected high or low bracket 12a or 12b, leaving plenty of room for bends to be placed into wires 18a and 18b.

The arrangement can work with self-ligating brackets, traditional brackets, or any other type of bracket desired. What is illustrated in the embodiment of FIG. 1 is the use of a split or two piece arch, which has the two wire segments 18a and 18b over lapping across the cuspids 28 and incisors 30 in the anterior segment. The wires 18a and 18b can be bent by a wire bending robot making the configuration of FIG. 1 a practical feasibility. The illustrated embodiment is the first known use of a double wire in the anterior segment, each wire 18a and 18b connected to every other tooth 16. It is to be understood that the bracket 12a and 12b is made small enough to fit on the upper or lower portion of the bonding pad 22.

Different designs for the bracket 12a and 12b may be employed to maximize the advantages of a double wire system 10, such as adjustable brackets 12a and 12b that include a sliding mechanism (not shown) to allow for connection in either a high or low position without the need to remount the bracket on the tooth 16. It is to be understood that the offset double wire system 10 of the illustrated embodiments may be adapted and employed with any design of brackets 14 or system of deployment of brackets 14 now known or later devised.

Figure 2:
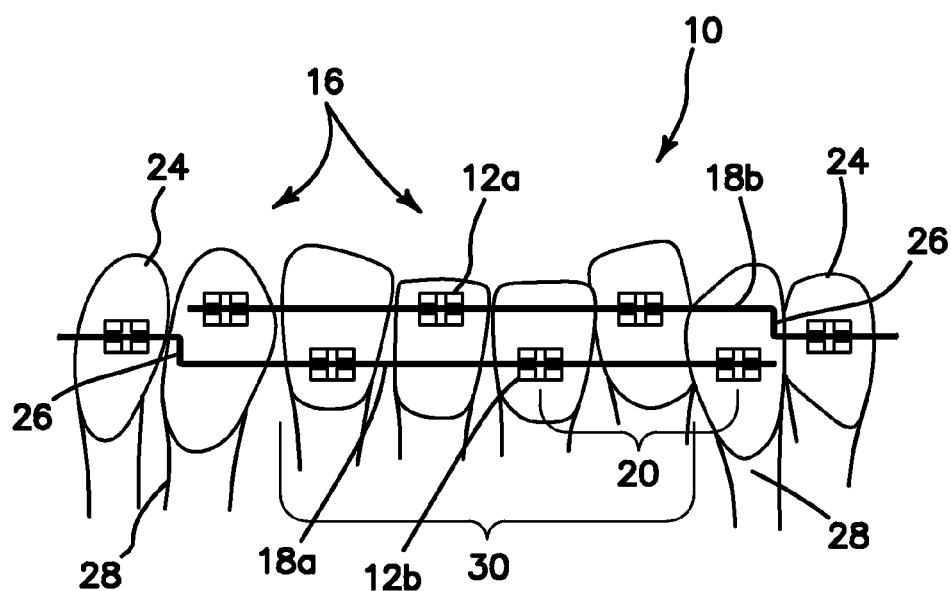
FIG. 2 is a diagram of an illustrated embodiment of the orthodontic bracket system of the invention showing its application to the lower anterior teeth, where the brackets on the lower anterior teeth from cuspid to cuspid are each place on either a high or low position directly onto the teeth instead of a bonding pad.

The illustrated embodiment also includes a compensating bend 26 in the double wires 18a and 18b between the cuspid 28 and premolar 24 to allow the high and low anterior segments of wires 18a and 18b to return to the plane common to the right and left posterior segments comprised of the right and left premolars 24 and molars (not shown) respectively. This is the plane that the wire 18a and 18b would be at if it were continuous and not higher, or lower as it crosses the incisors 30 and cuspids 28. In an alternative embodiment the brackets 14 are placed high or low on the alternate teeth 16 as shown in FIG. 2, as opposed to being placed differently on the pads 22 as shown in FIG. 1.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method of installing an orthodontic bracket system on anterior teeth, comprising:

fixing a subplurality of high brackets on an upper portion of every other anterior tooth and fixing a subplurality of low brackets on a lower portion of every other one of the remaining anterior teeth;

coupling a first orthodontic wire to the subplurality of high brackets and a second orthodontic wire to the subplurality of low brackets; and selectively bending the first orthodontic wire between the subplurality of high brackets and the second orthodontic wire between the subplurality of low brackets to which the first and second orthodontic wires are respectively coupled, so that the length of the first orthodontic wire between each of the subplurality of high brackets and the second orthodontic wire between each of the subplurality of low brackets is increased, leaving space between each of the subplurality of high brackets and each of the subplurality of low brackets for bends to be formed in the first orthodontic wire and the second orthodontic wire, respectively.

2. The method of claim 1 where coupling a first orthodontic wire to the subplurality of high brackets and a second orthodontic wire to the subplurality of low brackets comprises providing a split or two piece arch of two overlapping segments of the first and second orthodontic wires across an anterior segment of teeth.

3. The method of claim 1 further comprising fixing a bonding pad to each anterior tooth, and providing the subplurality of high brackets and subplurality of low brackets in a size arranged and configured to selectively be coupled on an upper or lower portion of the bonding pad fixed to each anterior tooth.

4. The method of claim 1 further comprising selectively forming a compensating bend in the first and second orthodontic wires between a cuspid of the anterior teeth and a premolar to allow a high and low anterior segment of the first and second orthodontic wires to return to a plane common to right and left posterior segments of the first and second orthodontic wires extending to right and left premolars and molars respectively.

5. The method of claim 1 where coupling a first orthodontic wire to the subplurality of high brackets and a second orthodontic wire to the subplurality of low brackets, and selectively bending the first and second orthodontic wires between the subplurality of high brackets and the subplurality of low brackets to which the first and second orthodontic wires are respectively coupled to comprises fixing the subplurality of high brackets and subplurality of low brackets at positions located high or low on alternate anterior teeth.

* * * * *